United States Patent
Di Maio

(10) Patent No.: US 11,759,493 B2
(45) Date of Patent: Sep. 19, 2023

(54) COMPOSITION FOR THE TREATMENT OF CONSTIPATION

(71) Applicant: NEILOS S.R.L., Piano di Sorrento (IT)

(72) Inventor: Umberto Di Maio, Piano di Sorrento (IT)

(73) Assignee: NEILOS S.R.L., Piano di Sorrento (IT)

( * ) Notice: Subject to any disclaimer, the term of this patent is extended or adjusted under 35 U.S.C. 154(b) by 319 days.

(21) Appl. No.: 16/650,921

(22) PCT Filed: Sep. 27, 2018

(86) PCT No.: PCT/EP2018/076212
§ 371 (c)(1),
(2) Date: Mar. 26, 2020

(87) PCT Pub. No.: WO2019/063666
PCT Pub. Date: Apr. 4, 2019

(65) Prior Publication Data
US 2020/0237843 A1    Jul. 30, 2020

(30) Foreign Application Priority Data

Sep. 27, 2017 (IT) .................. 102017000108033

(51) Int. Cl.
| | |
|---|---|
| A61K 36/72 | (2006.01) |
| A23L 33/105 | (2016.01) |
| A23L 33/125 | (2016.01) |
| A23L 33/00 | (2016.01) |
| A61K 31/7016 | (2006.01) |
| A61K 31/7032 | (2006.01) |

(52) U.S. Cl.
CPC .......... *A61K 36/72* (2013.01); *A23L 33/105* (2016.08); *A23L 33/125* (2016.08); *A23L 33/40* (2016.08); *A61K 31/7016* (2013.01); *A61K 31/7032* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 4,761,400 | A * | 8/1988 | Doat | .......... A61P 1/10 514/53 |
| 8,545,902 | B2 * | 10/2013 | Lion | .......... A61K 36/704 424/725 |
| 8,765,207 | B2 * | 7/2014 | Coles | .......... A23L 19/03 426/616 |
| 2005/0004155 | A1 | 1/2005 | Boyd et al. | |
| 2016/0100617 | A1 | 4/2016 | Roughead et al. | |
| 2017/0087150 | A1 | 3/2017 | Rey et al. | |

FOREIGN PATENT DOCUMENTS

| | | |
|---|---|---|
| EP | 0906109 A1 | 4/1999 |
| TW | 200930385 A | 7/2009 |
| WO | 9729755 A1 | 8/1997 |
| WO | 2009036906 A1 | 3/2009 |

OTHER PUBLICATIONS

International Search Report and Written Opinion for Corresponding International Application No. PCT/EP2018/079570 (12 Pages) (dated Dec. 11, 2018).
Loening-Baucke et al., Fiber (Glucomannan) Is Beneficial in the Treatment of Childhood Constipation, Pediatrics, 2004, vol. 113, No. 3, pp. e259-e264.
Fosini, "Stitichezza: ecco i rimedi naturali", URL:http://www.rodiola.info/stiticheza-rim edi-naturali.php, 2013, XP055476561, 2 pages.
"Assessment report on Plantago ovata Forssk., seminis tegumentum", EMA—European Medicines Agency, 2013, pp. 1-50.
International Search Report and Written Opinion for Corresponding International Application No. PCT/EP2018/076212 (12 Pages) (dated Nov. 7, 2018).

* cited by examiner

*Primary Examiner* — Terry A Mckelvey
*Assistant Examiner* — Catheryne Chen
(74) *Attorney, Agent, or Firm* — Lucas & Mercanti, LLP

(57) ABSTRACT

A composition containing a synergistic association of lactitol, lactulose and *Rhamnus frangula* extract for the treatment of constipation is described.

9 Claims, No Drawings

COMPOSITION FOR THE TREATMENT OF CONSTIPATION

The present invention refers to a composition containing an association of lactitol, lactulose and *Rhamnus frangula* extract for the treatment of constipation. The composition is particularly effective thanks to the synergistic action of its components.

BACKGROUND OF THE INVENTION

Constipation is a common gastrointestinal disorder which affects about 28% of the Western world population. Epidemiological studies demonstrate that this problem is mainly encountered in elderly, children and women and it deeply interferes with the life quality of said subjects.

In recent years several scientific studies have focused on researching an adequate definition for the term constipation on the basis of some parameters such as feces weight and consistency, time of colonic transit and evacuation difficulties.

The most important definitions refer to alterations of the above-mentioned parameters and constipation is mainly defined as a temporary or chronic condition wherein there is a delayed transit of feces in the intestine entailing infrequent, difficult or incomplete evacuations. This condition can cause pain and abdominal distention as well as anorexia and vomit and other less specific symptoms such as headache, halitosis, confusion, etc.

The causes of constipation are mainly three: lifestyle (functional constipation), secondary condition of other diseases or induced by the use of some drugs. According to the most valid criteria, functional constipation is defined and diagnosed as the presence of symptoms for three months with an onset thereof for at least six months.

The most specific diagnostic criteria are: straining during at least 25% of evacuations, hard and granulose feces for at least 25% of evacuations, sensation of incomplete evacuation for at least 25% of evacuations, sensation of anal blockage or obstruction for at least 25% of evacuations, the use of manual maneuvers to facilitate at least 25% of evacuations, fewer than three evacuations per week and rarely loss of feces.

The physiopathology of functional constipation, however, remains still not well clear but it is believed to be mainly due to a slow colonic transit and/or pelvic floor dysfunctions. As regards the colonic transit, this slowing can be due to either excessive segmental contractions or a reduced contraction of distal colon.

As mentioned before, the constipation may also be due to the use of some drugs and in this case it is referred to as iatrogenic constipation. Primarily, opioid analgesics can induce alterations of the intestinal functionality through their action on the central nervous system and mainly on the opioid receptors present at enteric level. Also anticholinergic drugs can induce constipation by blocking the acetylcholine receptors present at intestinal level. Also tricyclic antidepressants show the same mechanism as anticholinergics in potentially causing constipation. Diuretics, by reducing the absorption of water during the formation of feces or inhibiting the secretion, reduce intestinal motility and can lead to hypokalemia and constipation. Still other drugs that can cause constipation are antiparkinsonian agents, antihypertensives, MAOs inhibitors, antipsychotics, cholestyramine, etc.

Treatments usually performed in subjects suffering from this disorder vary according to the entity and cause of constipation. Initially, a conservative treatment comprising changes in diet and lifestyle, among which mostly a greater consumption of fibers, is preferred. In particular, in this regard reference is made to a consumption of about 30 g per day to ensures beneficial effects and prevent collateral events such as abdominal pain, flatulence and diarrhea.

Another common practice is the so-called biofeedback which can be useful in effectively coordinating the pelvic floor distention and the anal sphincter relaxation in order to facilitate the passage of feces.

When a simple variation in eating habits is not enough, pharmacological therapy is used which involves: bulk-forming laxatives and stool softeners, stimulant laxatives, osmotic laxatives, prokinetics and in the most serious cases enemas.

Bulk-forming laxatives have the same effect of fibers and include for example methylcellulose, psyllium and sterculia. These agents absorb water and increase the fecal mass promoting the frequency and consistency of feces.

Docusate instead is the main agent used to soften feces and its mechanism is linked to the ability to lower the surface tension of feces facilitating the entry of water.

Stimulant laxatives instead include plants containing anthraquinones (*senna, cascara, aloe, frangula, rhubarb*, etc.), diphenylamine derivatives (bisacodyl) and sodium picosulfate.

The use thereof is very common in both acute and chronic constipation and is linked to the ability to increase the intestinal motility and the secretion of water and electrolytes. Sodium picosulfate is mainly used for the preparation to endoscopy or other type of analysis.

Osmotic laxatives include magnesium and salts thereof, poorly absorbable sugars and polyethylene glycol-based preparations (PEG). These actives should represent the first line treatment to be followed in case the treatment with fibers or other changes in the lifestyle did not give the expected results. The mechanism of action thereof is linked to their ability to reach the colon in an unchanged manner establishing an osmotic gradient which increases fecal volume and peristalsis.

Prokinetic drugs are mainly cholinergic or serotonin 5-HT4 receptor agonists or of another type such as erythromycin, domperidone and metoclopramide.

The cholinergic agonists which are mostly recommended are bethanechol (25-50 mg 3 to 4 times a day reduces the constipation induced by tricyclic antidepressants) and neostigmine even if there are no significant scientific studies in support.

Among the 5-HT4 receptor agonists the main one is prucalopride which is recommended if the use of other types of laxatives has not brought about the desired effect. The use at a dosage between 1 and 2 mg increases the intestinal motility and decreases the time of colonic transit.

Moreover, also opioid receptor antagonists can be used in the treatment of constipation. US 2017/087150, for example, discloses prolonged release dosage forms comprising naloxone or a derivative thereof for the treatment of opioid induced constipation.

Now it has been surprisingly found that an association of lactitol, lactulose and *Rhamnus frangula* extract is particularly effective in the treatment of constipation thanks to to the synergistic action of its components.

DETAILED DESCRIPTION OF THE INVENTION

Therefore, an object of the present invention is a composition containing an association of lactitol, lactulose and *Rhamnus frangula* extract useful for the treatment of constipation.

The components of the association according to the present invention are all known components, widely used in therapy.

Lactitol

Lactitol, usually marketed in monohydrate form, is a disaccharide polyol composed of galactose and sorbitol units. Its chemical formula is $C_{12}H_{24}O_{11}$ and it is identified with the chemical name 4-O-β-D-galactopyranosyl-D-glucitol. Lactitol is obtained by catalytic hydrogenation of lactose from cow's milk affording an about 95% pure product. This polyol is approved by the European Union as food additive with the code E966 and used as synthetic sweetener.

Recently, the EFSA has received a positive opinion about the use of lactitol to obtain a normal intestinal functionality increasing the defecation frequency, feces consistency and water content also reducing the time of intestinal transit.

This effect is surely justified by numerous clinical studies that were carried out on lactitol to evaluate a potential use thereof in the treatment of constipation.

Lactitol exerts these beneficial actions thanks to its intrinsic characteristics: in fact being a non-digestible sugar, firstly, it reaches in an unchanged manner the intestine wherein by osmotic effect it recalls huge amounts of water. Moreover, it is fermented and in this way it could increase the feces volume and reduce the permanence time in the colon. It is known that said conditions are related to each other and facilitate defecation. From the fermentation of lactitol, acids (lactic acid) which contribute to maintain low the pH of bacterial flora, gas and short chain fatty acids (SCFAs), which could have a direct effect on the colonic motility, are formed.

As mentioned before, different clinical studies relative to lactitol administration in adults compared with both the placebo and lactulose or with other types of laxatives have been performed.

On the basis of a recent 2014 meta-analysis, it has emerged, from the analysis of the different clinical studies, that lactitol is well tolerate and is able to increase the evacuation frequency and the feces consistency in patients affected by constipation.

In particular, relative to the comparative studies with lactulose, one of the active ingredients most used and requested by patients with constipation, lactitol has shown a comparable efficacy and tolerability with a favorable trend for lactitol relatively to the evacuation frequency. Moreover, some studies report a better palatability and taste of products containing lactitol with respect to those containing lactulose, which could reduce some of the gastrointestinal symptoms and increase patient compliance. This effect is probably due to the low glycemic index of lactitol which ensures an intake of only 2 calorie/g unlike other sugars. In fact, in marketed lactitol-based products, reference is made to the possibility of usage in diabetics as this disaccharide has no effects on glycaemia and insulinaemia.

In particular, EP 0 906 109 discloses an aqueous laxative syrup comprising lactulose and lactitol, wherein lactitol is merely used to improve the palatability (in terms of taste and viscosity) of said syrup.

Regarding the dosages and the safety of use, in general, lactitol-based formulations have proven to be effective and safe (without side effects such as diarrhea or abdominal pain typically) at a dosage of 10 g per day. In fact several studies report the absence of diarrhea at this dosage while a percentage between 5-20% of people involved in the studies were affected by diarrhea, in case of using 20 g of active ingredient.

Lactulose

Lactulose is a disaccharide composed of fructose and galactose which usually is not present in milk but derives from heating processes; in fact, as the heating temperature increases a higher yield of this sugar is always obtained. It is commercially produced by reduction of lactose.

Lactulose is one of the active ingredients mostly used for the treatment of constipation which over the years has always maintained a good efficacy/safety profile.

This active is not absorbed in the gastrointestinal tract reaching in an unchanged form the colon where it performs its effect through osmotic action.

The lactulose action of increasing the intestinal transit by enhancing the evacuation has been demonstrated by some clinical studies that certify its efficacy and by the wide use over the years.

A first study carried out on 42 healthy volunteers and 24 subjects suffering from constipation assessed the effect of the administration of 20 and 40 g of lactulose per day. The results of the double-blind study have registered a significant increase of the frequency, volume and weight of feces in both the study groups.

Another 1997 study assessed the effect of 10 g of lactulose with respect to the placebo to evaluate the oro-fecal transit in eight healthy individuals confirming an accelerating effect of the transit in the small intestine. Lactulose if compared to inulin has also proved to be effective in accelerating the transit when taken at a dosage of 10 g per day.

These data confirm the dated use of lactulose in the treatment of constipation. In fact, within the colon, lactulose is degraded into lactic acid, small amounts of acetic and formic acid through the action of beta-galactosidases of the bacterial flora. This process causes an increase in the osmotic pressure and a slight acidification of the colonic content which causes an increase in the water content in the feces which softens them making the defecation easier.

In case of particularly high dosages or use for prolonged periods of time, lactulose can causes light and transitional side effects such as flatulence, bloating and nausea. Despite these light side effects the efficacy/safety ratio for this active is anyway high which is why lactulose represents a valid active ingredient to be used as a medicinal or nutraceutical product for the treatment of constipation.

Rhamnus frangula

*Rhamnus frangula* or *Frangula alnus*, also known with the name of alder buckthorn, glossy buckthorn or breaking buckthorn, is a deciduous shrub belonging to the family of Rhamnaceae.

The drug of the plant is the cortex from which anthraquinone active ingredients such as mainly glucofrangulin A are extracted. In the cortex small quantities of aglycones such as emodin and emodin-9-anthrone are also present.

*Frangula* belongs to the family of stimulant laxatives and emodin-9-anthrone is the main metabolite produced by the bacteria at intestinal level. The mechanism of action is attributable to two different actions: first of all there is an increase in the colonic motility leading to a reduction of the transit in the colon which is usually slowed down in patients affected by constipation. Secondly, *frangula* anthraquinones influence the secretion process by inhibiting the absorption of water and electrolytes in colonic epithelial cells increasing the resistance of the tight junctions and stimulating the secretion of water and electrolytes ($Na^+$ e $Cl^-$) in the colon lumen.

The use of this plant is considerably dated: in fact even the first 1996 studies reported the superior effect of glucofrangulin and frangulin compared to the extract of *senna* leaves.

From in vivo studies on mice the extract of the plant cortex with an anthraquinone glycosides titre of 17.5% reduced the time of intestinal transit and after an administration a defecation occurred after 4 hours in a dose-dependent manner. As reported in the plant monograph by the EMA, the administration in human of an aqueous suspension containing the equivalent of 12 mg of anthraquinone derivatives (glucofrangulin and frangulin) had a laxative effect in the following 6 to 24 hours.

In the literature there are no clinical studies exclusively relating to the administration of frangula extracts but only in combination with other active ingredients. One of these studies assessed the effect of a formulation (Laxariston) containing methylcellulose (0.9 g), extract of *senna* leaves (corresponding to 7.5 mg of hydroxyanthracene derivatives), extract of *rhubarb* root (equal to 6.75 mg of hydroxyanthracene derivatives), 15 mg of *Achillea* extract and extract of *frangula* cortex containing an amount of hydroxyanthracene derivatives equal to 13.5 mg. From the results of the study carried out on patients with arthritis or who had undergone abdominal surgery or with functional constipation, the product had a very positive efficacy in 77% of patients with a good tolerance. Another subsequent study evaluated the same product in 95 pregnant women suffering from constipation with an ameliorative result on 55 women of the treated group with a low percentage of side effects. It is worth noting also how out of a total of 27.75 mg of hydroxyanthracene derivatives within the daily dosage of the product, about 50% derives from frangula therefore the contribution to the final laxative effect can be significantly supported.

As recommended, the consumption of hydroxyanthracene derivatives should never exceed the dosage of 20-30 mg per day for no longer than 1-2 weeks in order to avoid the onset of side effects. For said reasons the frangula extract by promoting intestinal motility and improving evacuation frequency, thanks to the presence of glucofrangulin and frangulin, represents a valid active ingredient for the treatment of constipation in adults.

In a preferred embodiment, the composition object of the present invention comprises the association of lactitol, lactulose and *Rhamnus frangula* extract, in admixture with a suitable acceptable carrier.

Suitable acceptable carriers are those commonly known to the man skilled in the art for the preparation of compositions for oral administration such as solutions, suspensions, powders or granulates, tablets, capsules, pellets. By way of non-limiting example, said acceptable carriers can consists of binders, diluents, lubricants, glidants, disintegrants, solubilizing (wetting) agents, stabilizers, colorants, anti-caking agents, emulsifiers, thickeners and gelling agents, coating agents, humectants, sequestrants, and sweeteners.

Specifically examples of diluents can be: magnesium carbonate, cellulose microcrystalline, starch, lactose, and sucrose; mainly used lubricants are magnesium stearate, stearic acid, and sodium stearyl fumarate. As glidants colloidal silica and magnesium silicate, as disintegrants the cross-linked polyvinylpyrrolidones, and sodium starch glycolate, as solubilizing agents surfactants such as TWEEN or sodium lauryl sulphate, and as stabilizers all classes of preservatives (sorbic acid and derivatives, benzoic acid and derivatives, parabens), antioxidants (ascorbic acid and derivatives, tocopherol), and acidifying agents (phosphoric acid, tartaric acid) can be cited. Thickeners and gelling agents can be carrageenan, pectins, and starches, coating agents include for example waxes and derivatives, anti-caking agents include for example calcium or magnesium carbonate, humectants include for example sorbitol and mannitol, sequestrants include for example EDTA and derivatives, sweeteners include for example aspartame, and acesulfame potassium.

The composition object of the present invention is preferably a liquid or solid composition for oral use, even more preferably an aqueous solution, a suspension, a powder or granulate, a tablet, a capsule, a pellet.

The composition of the present invention can be a medical device, a food supplement, a nutraceutical, dietetic and nutritional composition, a food product, a beverage, a nutraceutical product, a medicament, a medicated food, a pharmaceutical composition or a food for special medical purposes.

The composition object of the present invention contains lactitol, lactulose and *Rhamnus frangula* extract.

Lactitol is present in an amount between 400 mg and 30 g, preferably between 1 g e 10 g, still more preferably between 5 g and 10 g.

Lactulose is present in an amount between 400 mg and 30 g, preferably between 1 g e 10 g, still more preferably between 4 and 5 g.

*Rhamnus frangula* extract is present preferably as a dry or liquid extract in an amount between 10 mg and 1500 mg, preferably between 50 mg and 1000 mg, still more preferably between 100 mg and 600 mg.

Preferably a dry extract of the plant cortex with known titration in anthraquinones/hydroxyanthracene derivatives is used.

The compositions object of the present invention are particularly effective in the treatment of constipation allowing to obtain at the same time the stimulation of intestinal motility and the increase in the frequency, weight and consistency of feces thanks to the synergistic action of their components.

Therefore a further object of the present invention is a composition containing the association of lactitol, lactulose and *Rhamnus frangula* extract in admixture with a suitable acceptable carrier for use in the treatment of constipation.

Without being bound to a specific theory, the inventors are of the opinion that the synergistic effect of the association of lactitol, lactulose and *Rhamnus frangula* extract, according to the present invention, derives from the following activities of the components of the association.

Lactitol and lactulose are non-absorbable disaccharides which reach in an unchanged form the colon where they are fermented by bacterial flora entailing a water recall through osmotic effect and simultaneously ensuring an adequate pH of intestinal bacterial flora crucial for the growth of beneficial microorganisms (lactobacilli and bifidobacteria).

*Rhamnus frangula* extract, thanks to the presence of metabolites such as glucofrangulin and frangulin, is able to increase the intestinal motility and enhance the secretion of water and electrolytes in the colon lumen in order to facilitate the evacuation.

The efficacy of the composition object of the present invention is evaluated with the following experimental protocol.

Constipation is induced through the administration to animals (mice and rats, preferably mice) of compounds such as loperamide (3 mg/Kg) which binds to $\mu$, $\kappa$ and $\delta$ receptors leading to a reduction of muscle contractility at intestinal level and a reduction of secretions. Moreover said drug increases the absorption of water and reduces the contraction of sphincters reducing the evacuation frequency. Also other compounds that induce this type of effects or variation in diet (such as diets rich in fibers or with a high protein content) can anyway be used as experimental model of constipation.

After the induction of constipation, the compositions according to the present invention and the comparative compositions are orally administered to animals at established dosages comparing them with a control group normally administered with a saline solution or however an inert substance. To evaluate the potential laxative effect, the feces of animals are collected every day for a variable period of time.

From the excreted feces, the number, the consistency in terms of weight and the water content (%), which is obtained from the ratio between wet feces weight minus dried feces weight divided by wet feces weight all multiplied by one hundred, are determined.

Another test that can be performed to assess the potential laxative action in terms of increase of intestinal motility is the study of the intestinal transit that is usually performed through the administration of coal or other similar compounds to animals after loperamide administration. Successively to constipation induction, animals are maintained without food in cages with wide meshes to facilitate feces fall.

After the administration (preferably after 30 minutes) of the compositions according to the present invention, or of the comparative compositions, animals are administered with a suspension (containing agents such as methylcellulose or preferably gum arabic) of coal (for example at 3-10%). After about 20-30 minutes the animals are sacrificed and the percentage of coal transit is obtained from the following equation:

total length of small intestine−distance covered by the coal/total length of small intestine*100

Moreover, the synergistic effect of the composition can be highlighted evaluating the propulsion in the distal colon after six days from loperamide administration. Thirty minutes after samples administration (or the control and the vehicle), a glass pearl of 3 mm is inserted through the anus in the distal colon for 2 cm. For each animal the medium expulsion time (MET) of the glass pearl will be evaluated; an high MET value indicates an elevated reduction of the intestinal motility.

Using the above-described experimental protocols, the laxative action of the association of lactitol, lactulose and *Rhamnus frangula* extract, according to the present invention, and of the individual components of the association is evaluate to verify the synergistic effect.

EXAMPLES

By way of example are now provided some non-binding examples of daily doses of active components of the composition object of the present invention.

Daily doses are meant to be administrated in a suitable oral dosage form and divided in one or more dosage units.

Example 1

Powder or Granulate for Oral Use

| Active ingredient | Daily dose amount |
| --- | --- |
| *Rhamnus frangula* dry extract | 200 mg |
| Lactitol | 10 g |
| Lactulose | 4 g |

Example 2

Powder or Granulate for Oral Use

| Active ingredient | Daily dose amount |
| --- | --- |
| *Rhamnus frangula* dry extract | 600 mg |
| Lactitol | 5 g |
| Lactulose | 5 g |

Example 3

Oral Solution

| Active ingredient | Amount in 20 mL (daily dose) |
| --- | --- |
| *Rhamnus frangula* dry extract | 300 mg |
| Lactitol | 10 g |
| Lactulose | 4 g |
| Potassium sorbate | 15 mg |
| Sodium benzoate | 15 mg |
| Xanthan gum | 15 mg |
| Flavouring agent | 5 mg |
| Water | q.s. to 15 mL |

The oral solution is prepared by conventional techniques such as mixing.

The invention claimed is:

1. A composition comprising lactitol, lactulose and *Rhamnus frangula* extract in admixture with a suitable acceptable carrier,
   wherein lactitol is present in an amount between 1 g and 10 g;
   wherein lactulose is present in an amount between 1 g and 10 g; and
   wherein the *Rhamnus frangula* extract is present in an amount between 50 mg and 1000 mg.

2. The composition according to claim 1 in the form of a liquid or solid composition for oral use.

3. The composition according to claim 2 in the form of aqueous solution, suspension, powder, granulate, capsule, tablet, or pellet.

4. The composition according to claim 1 wherein the *Rhamnus frangula* extract is a dry or fluid extract.

5. The composition according to claim 1 wherein the composition is a medical device, a food supplement, a nutraceutical, dietetic and nutritional composition, a food product, a beverage, a nutraceutical product, a medicament, a medicated food, or a pharmaceutical composition.

6. The composition according to claim 1 wherein lactitol is present in an amount between 5 g and 10 g.

7. The composition according to claim 1 wherein lactulose is present in an amount between 4 g and 5 g.

8. The composition according to claim 1 wherein the *Rhamnus frangula* extract is present in an amount between 100 mg and 600 mg.

9. A method of treating constipation, comprising administering a composition of claim 1 to a patient in need thereof.

\* \* \* \* \*